(12) United States Patent
Backus et al.

(10) Patent No.: US 8,004,292 B1
(45) Date of Patent: Aug. 23, 2011

(54) ELECTRICAL PENETRATION GRAPH SYSTEM

(75) Inventors: Elaine Backus, Clovis, CA (US); William Bennett, Otterville, MO (US)

(73) Assignee: The United States of America, as Represented by the Secretary of Agriculture, Washington, DC (US)

(*) Notice: Subject to any disclaimer, the term of this patent is extended or adjusted under 35 U.S.C. 154(b) by 485 days.

(21) Appl. No.: 12/256,168

(22) Filed: Oct. 22, 2008

(51) Int. Cl.
*G01R 27/08* (2006.01)
(52) U.S. Cl. .................................. 324/692; 324/691
(58) Field of Classification Search .............. None
See application file for complete search history.

(56) References Cited

U.S. PATENT DOCUMENTS 6,304,185 B1 * 10/2001 Tuttle et al. ................ 340/573.2
7,084,640 B2 * 8/2006 Berhorst et al. ............ 324/611

OTHER PUBLICATIONS

Backus, Elaine A., "History, Development, and Applications of the AC Electronic Monitoring System for Insect Feeding," Thomas Say Publications: Electronic Feeding Monitors, pp. 1-51, 1994.
Walker, G. P. et al., "A Beginner's Guide to Electronic Monitoring of Homopteran Probing Behavior," Thomas Say Publication in Entomology: Proceedings, pp. 14-40, 2000.

* cited by examiner

*Primary Examiner* — Vinh P Nguyen
(74) *Attorney, Agent, or Firm* — John D. Fado; Robert D. Jones

(57) ABSTRACT

An electrical penetration graph (EPG) system includes a monitoring device with a buffered and stabilized voltage source assembly and a buffered internal amplifier with switched gain control. The system also includes a head stage amplifier. During the EPG process, the voltage source assembly directs an electrical current through a feeding insect. As the current passes through the insect, the insect's feeding process modulates the current and creates voltage waveform data. A head stage amplifier with selectable input resistance receives and amplifies the voltage waveform data. The data is transmitted back to the monitoring device where it is manipulated and further amplified by the monitoring device internal amplifier assembly. The waveform data is then transmitted to a controller and ultimately to an output device where the data is displayed.

31 Claims, 8 Drawing Sheets

ELECTRICAL PENETRATION GRAPH SYSTEM

FIELD OF THE INVENTION

The current invention relates to an improved electrical penetration graph (EPG) monitoring system.

BACKGROUND OF THE INVENTION

The current invention was designed to record the feeding processes of aphids and other soft-bodied, piercing-sucking agricultural pests. These insects spread numerous, deleterious plant viruses that cause many millions of dollars in damage to crops worldwide every year.

Aphids and other piercing-sucking insects acquire plant pathogens from infected plants and inoculate them to healthy plants. After aphids acquire the pathogens, it remains in the insect's body throughout its life. Researchers (including the inventors) are attempting to combat these plant diseases by better understanding how aphids and other vectors of plant pathogens carry and spread the pathogen via their feeding processes.

One means of studying the transmission of the disease is through an understanding of the way the insects feed. Direct current electrical penetration graph (EPG) technology provides information regarding the way that the insect draws its fluid food from plants. The EPG process is initiated by attaching a gold wire to the body of a sharpshooter and placing the sharpshooter in a feeding position on the leaf of a host plant. A plant electrode is then placed in the soil adjacent to the plant or attached directly to a part of the plant. A lead wire from the plant electrode and the gold wire attached to the insect are then connected to a monitoring device.

When the stylets (the probing and penetrating mouth parts of the insect) connect with the host plant, an electrical circuit is completed. As the insect's stylets probe the host plant, the voltage in the circuit fluctuates. The voltage fluctuations are depicted as waveform data on a computer monitor or on a time-based chart in a similar manner to an electrocardiogram (EKG) chart. Researchers have been able to correlate the waveform data (i.e. voltage fluctuations) with certain feeding activities to better understand the biological mechanisms that facilitate the spread of the *Xylella fastidiosa* bacteria.

Although the hardware associated with the direct current EPG monitoring process has been around since the 1970s, no meaningful update of the monitoring system design has apparently been attempted since its inception. The currently available monitor has been marketed under the name "Giga 8" or "Giga8", although a cursory search of the US Patent and Trademark Office, Trademark Electronic Search System indicates that neither name is trademarked in the US.

The Giga 8 is a direct current EPG monitor that was originally designed primarily for aphids and other small piercing-sucking insects. Aphids are very tolerant of direct current excitation signals and consequently direct current EPG monitors continue to be used to study aphids. However, even for these direct current tolerant insects, the Giga 8 is no longer sufficiently suited for scientific inquiry. The direct current EPG system of the current invention eliminates several problems with the Giga 8, and also expands its usefulness for other, direct current-tolerant insects, especially larger insects such as large leafhoppers and heteropterans.

Among other things, the excitation voltage source of the Giga 8 is unregulated and uncompensated. The excitation control potentiometer has a negative DC voltage applied to one end of a fixed resistance element and a positive voltage applied to the other. Further, the excitation voltage cannot be precisely and reproducibly set. No means is available to determine the actual excitation voltage selected because the instrument is not capable of calibration. The excitation voltage is fed directly out from the control potentiometer wiper, without compensation to stabilize the voltage at any set level and the instrument has no index or dial settings available for reference and adjustment.

Although the Giga8 has a head stage amplifier (i.e. "head amp"), the head amp is limited to a single, fixed input resistance setting. This severely limits the sensitivity of the Giga 8, making it only useful for aphids and closely related insects. The main internal amplifier of the Giga 8 has a very low gain. This is not problematic for the small range of insect species that it was designed to monitor, but the Giga 8 design limits the instrument's ability to study other species of arthropod.

Further, as with other aspects of the Giga 8, the gain control has no scale. An operator simply arbitrarily adjusts the gain control until he/she is satisfied with the result. Consequently there is no means of documenting the exact instrument settings associated with the produced waveform data, therefore the results obtained from an evaluation using the Giga 8 are not precisely reproducible and verifiable by other researchers.

As indicated above, most of the electronic components of the Giga 8 are obsolete. For example, the Giga 8 operational amplifier is a µA741, which was designed in the 1970's. It has a very limited ability to change the output voltage to follow the input signal (i.e. slew rate). At even a moderate gain, the output may not closely resemble the shape of the input waveform, especially when the amplitude changes rapidly. Thus, output signals may be inaccurate and artifactual.

Because of the limitations described supra, the Giga 8 is only marginally useful. The need exists for a new EPG monitor that includes updated components as well as a wider range of applicability.

The current invention provides an EPG monitoring system that includes the ability to produce more detailed, accurate, and higher-resolution waveforms than the prior art system. The EPG monitoring system of the current invention also provides switchable amplifier sensitivities and expands the utility of the direct current EPG process to essentially all direct current-tolerant piercing-sucking arthropods.

SUMMARY OF THE INVENTION

The current invention is directed to a system for monitoring the feeding behavior of insects. Current is directed from a regulated and buffered voltage source in a monitoring device to an insect electrode that is attached to an insect feeding on a host plant. The current travels through the insect and is picked up by a head stage amplifier system. The head stage amplifier system is comprised of an operational amplifier assembly and a switched resistor assembly. The switched resistor assembly is comprised of multiple selectable resistors yielding multiple selectable levels of input resistance for the head stage amplifier. A resistance selection means such as a switch or rotary dial enables an operator to select one of the selectable resistors and thereby specify an input resistance for the head stage amplifier.

The head stage amplifier transmits a waveform voltage signal back to a buffered internal amplifier within the monitoring device. The internal amplifier is essentially comprised of a chain of operational amplifiers that include input and output buffers and allow an operator to adjust the gain and offset of the of the waveform signal.

In operation, an operator initiates an evaluation of an insect by connecting the insect to an insect electrode and placing the insect in a feeding position on a host plant. Current is directed from the voltage source in the monitoring device, through the feeding insect to the head stage amplifier. The feeding insect modulates the current so that a waveform voltage signal is received by the head stage amplifier. The head stage amplifier amplifies the waveform voltage signal and transmits the signal back to an internal amplifier in the monitoring device. The monitoring device ultimately transmits the signal to a display device so that the waveform voltage signal can be examined by researchers.

DETAILED DESCRIPTION OF PREFERRED EMBODIMENTS

The present invention is directed to an improved direct current electrical penetration graph (EPG) system for studying insect feeding behavior. In the preferred embodiment, the current invention is used to study the feeding behavior of aphids and small leafhoppers, although the system may be used to study a wide range of other insects.

Figure 1:
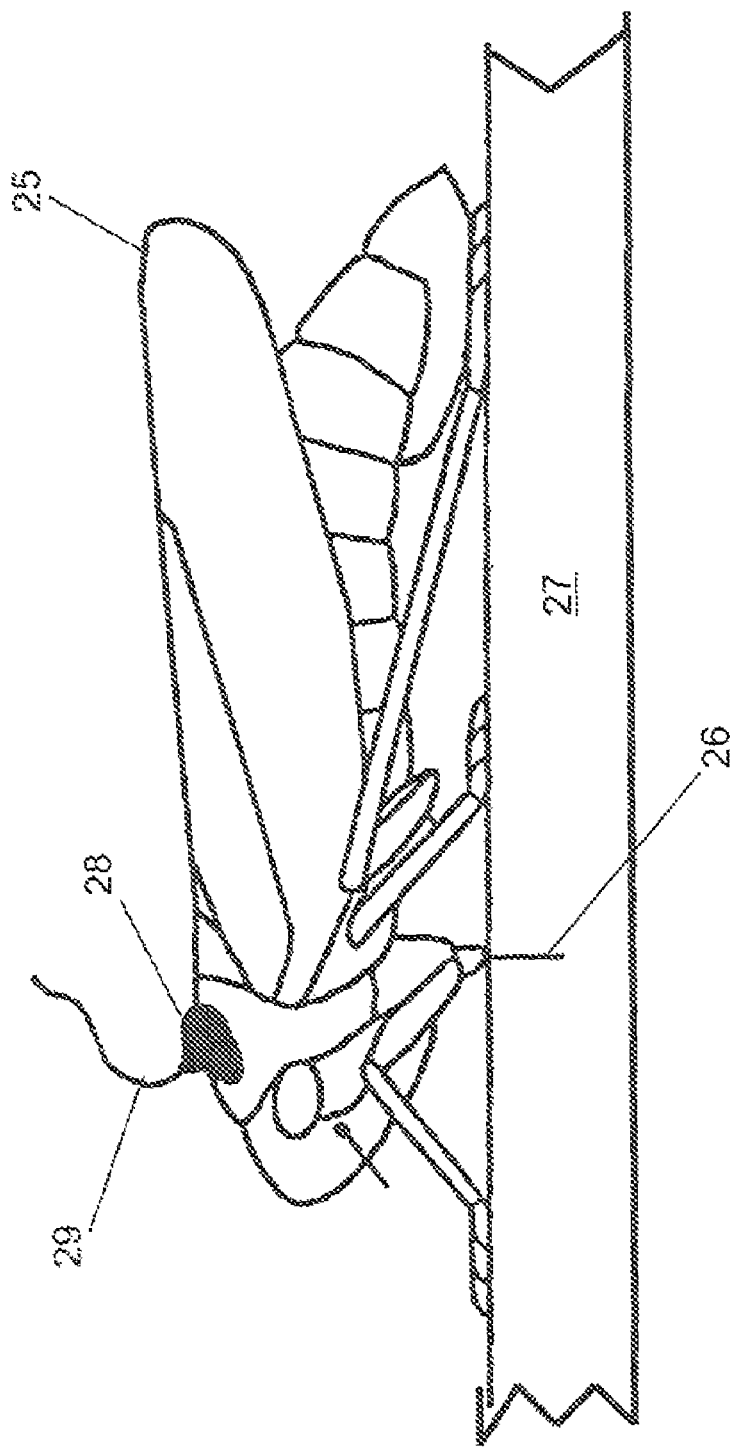
FIG. 1 is a leaf hopper with an electrode attached.

As generally shown in FIG. 1, a leafhopper 25 feeds on a host plant 27 by inserting its mouthparts (i.e. "stylets") 26 into the leaf of the host plant 27. An electrode 28 is attached to the head of the insect 25 and a thin gold wire 29 is attached to the electrode 28.

Figure 2:
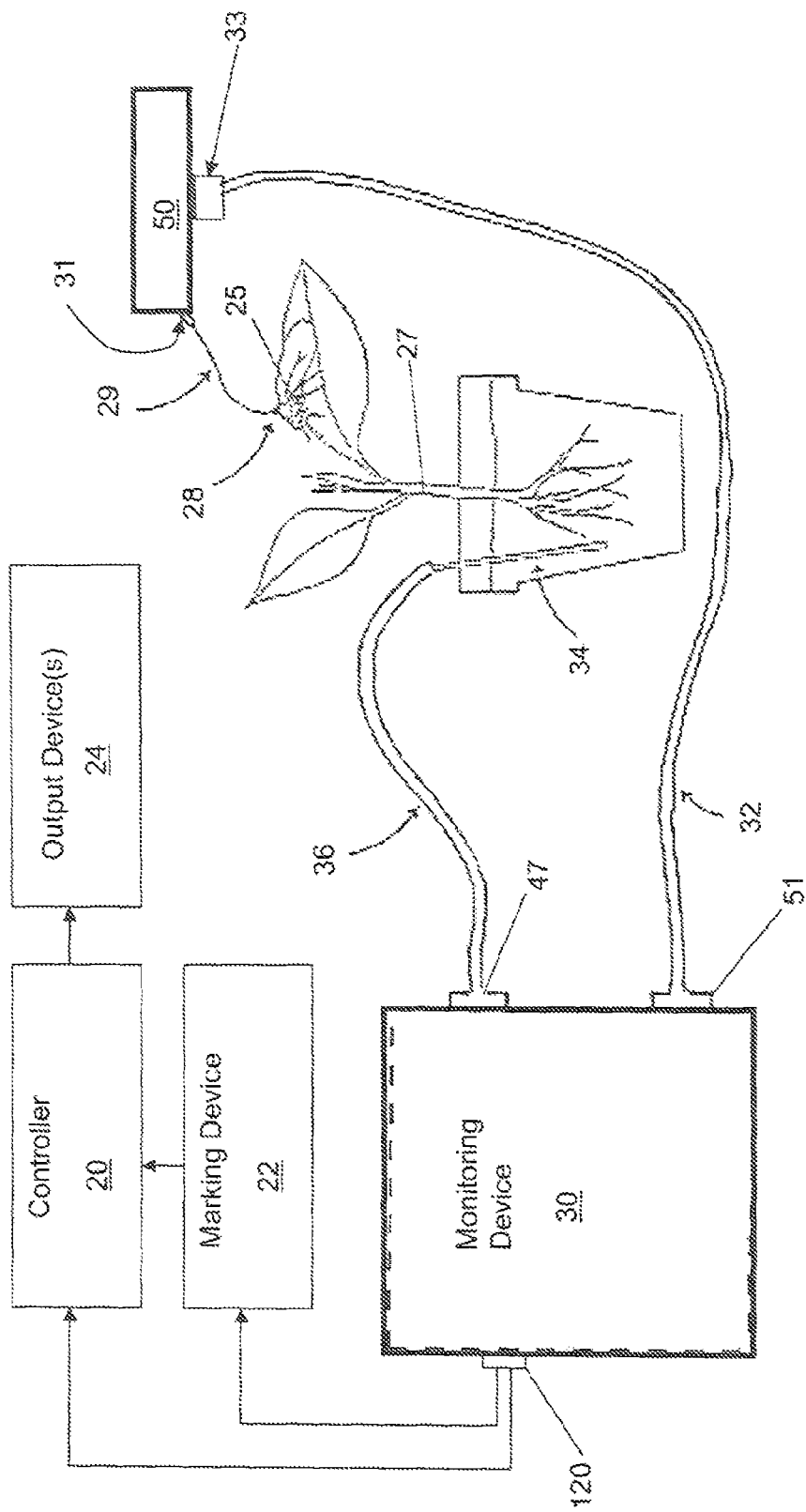
FIG. 2 depicts a leaf hopper connected to the monitoring system of the current invention.

As generally shown in FIG. 2, the thin gold wire 29 attaches the insect 25 and the electrode 28 to a head stage amplifier system (i.e. "head amp" system) 50 through an input terminal 31. A head amp cable 32 attaches the head amp system 50 to a monitoring device 30. A plant electrode 34 is attached to the host plant 27 or inserted in the soil adjacent to the host plant 27. A plant electrode cable 36 attaches the host plant electrode 34 to the monitoring device 30.

In the preferred embodiment, a portion of the signal generated by the monitoring device 30 is directed from the monitoring device 30 to a marking device 22 and then to a controller 20, and a portion of the signal is sent directly to the controller 20. The controller 20 transmits the signal to one or more output devices 24. These output devices 24 may include computer display screens, video monitors, printers, and the like. In alternative embodiments, the signal from the EPG monitoring device 30 may be sent directly to a display or to any other device(s) specified by an operator. The marking device 22 is the subject of a patent application previously filed by the current inventors.

Although the EPG process is generally known in the prior art, the current invention includes significant improvements to the prior art system. Specifically, the current invention comprises: (a) an improved EPG voltage source assembly 40 (housed in the monitoring device 30) so that the voltage applied to the system is consistent, reproducible, reliable, and accurate; (b) an improved head amp system 50 so that the EPG process is sensitive enough to accurately relay subtle changes in the detected waveforms, and so that a greater range of insects can be evaluated, and (c) an improved internal amplifier assembly 80 (housed in the monitoring device 30) to allow for further adjustment as well as clear and accurate transmission of the waveform signal.

Figure 3:
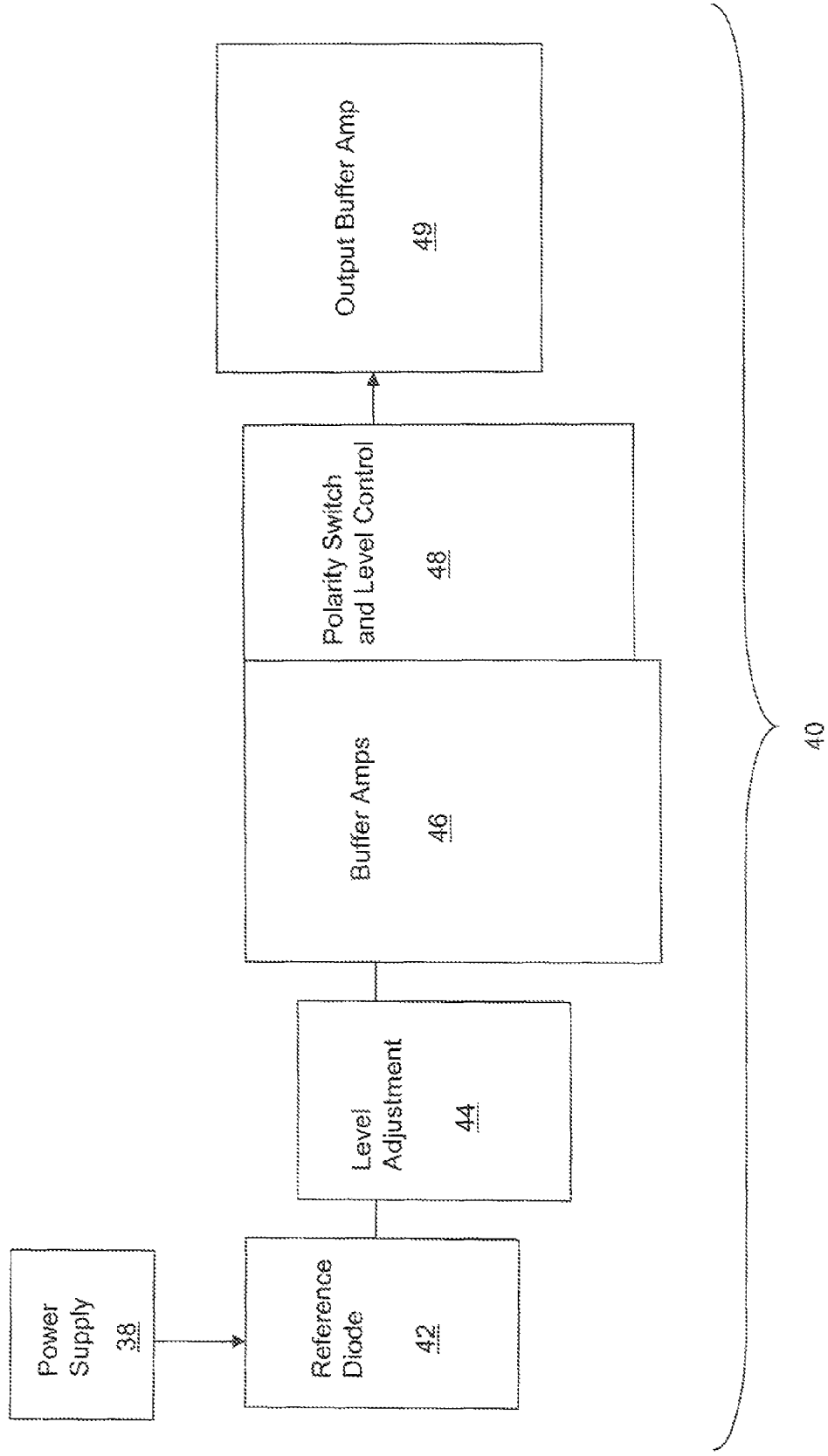
FIG. 3 is a block diagram of the voltage source for the monitoring system.
Figure 4:
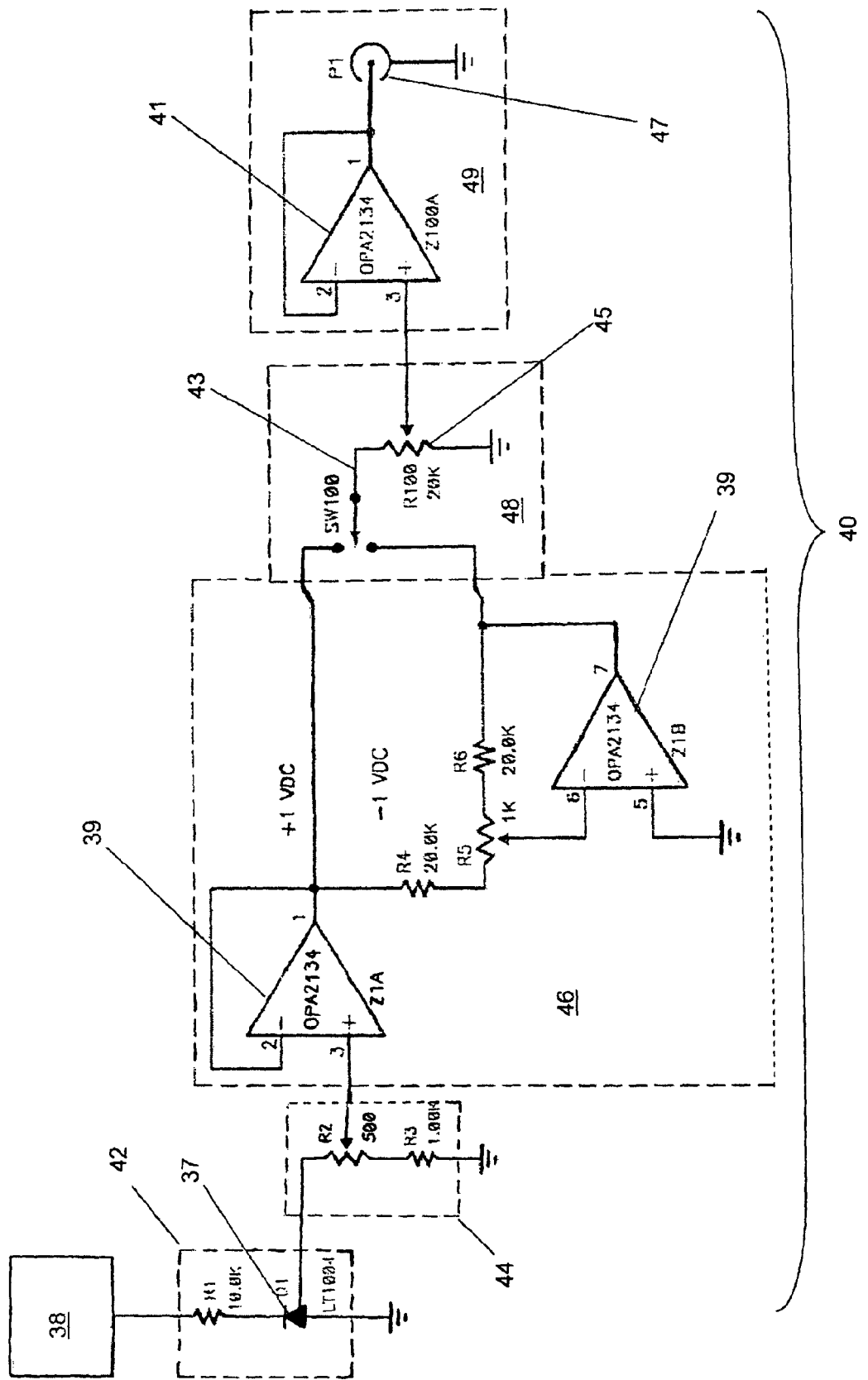
FIG. 4 is a circuit diagram of the voltage source shown in FIG. 3.

As shown in FIGS. 3 and 4, the voltage source assembly 40 of the current invention allows an operator to selectively specify whether a positive or a negative voltage is applied to the system substrate. In the preferred embodiment, the substrate is comprised of the material between the insect electrode 28 and the plant electrode 34. Because of the relatively small amounts of current, precise control of the system voltage is critical.

The voltage source assembly 40 is powered by a 12 volt direct current (DC) power source 38. Current flows from the power supply 38 to a reference diode assembly 42 that is connected to an internal level adjustment (i.e. potentiometer) 44, an input buffer amplifier assembly 46, and an externally adjustable polarity switch assembly 48. As shown in FIG. 4, within the polarity switch assembly 48, a polarity switch component 43 (designated SW100 in FIG. 4) allows an operator to select either a positive or negative voltage.

As further shown in FIG. 4, the voltage source assembly 40 voltage can be further fine-tuned through manipulation of a variable resistor component 45 (designated R100 in FIG. 4). In the preferred embodiment, a switch associated with the polarity switch component 43 and a dial associated with variable resistor component 45 are disposed on the outside of the monitoring device 30 shown in FIG. 2 so that the settings are easily adjustable by an operator.

As best shown in FIG. 4, the variable resistor component 45 is connected to an output buffer amplifier assembly 49 that buffers the output voltage. The output buffer amplifier assembly 49 is connected to an output terminal 47. As best shown in FIG. 2, the output terminal 47 is connected to the plant electrode cable 36 which delivers power from the voltage source assembly 40 to the plant electrode 34.

As shown in FIG. 4, in the preferred embodiment, the reference diode component 37 is comprised of an LT1004-type component. The operational amplifiers 39 in the input buffer assemblies 46 are comprised of OPA2134-type components. The amplifier 41 in the output buffer amplifier assembly 49 is also comprised of an OPA2134-type component. In alternative embodiments, these components 37, 39, 41 may be comprised of any type of device consistent with the function as described herein. As shown in FIG. 2, the current invention also includes an updated and improved head amp system 50. As best shown in FIG. 2, the head amp system 50 is positioned near the insect 25 and host plant 27. The gold wire tether 29 connects the head amp 50 with the insect electrode 28 through an input terminal 31.

Figure 5:
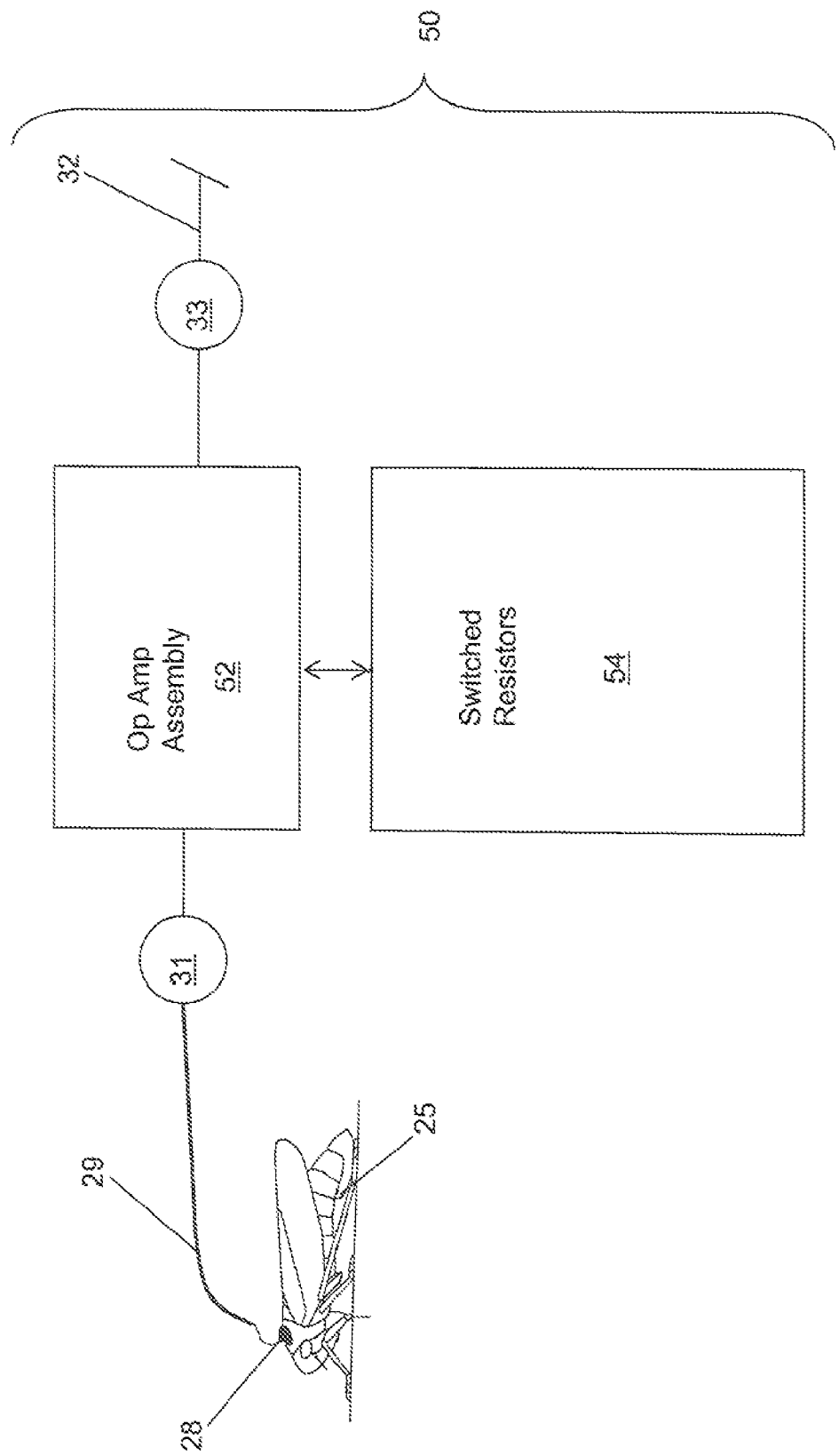
FIG. 5 is a block diagram of the head stage amplifier of the monitoring system.
Figure 6:
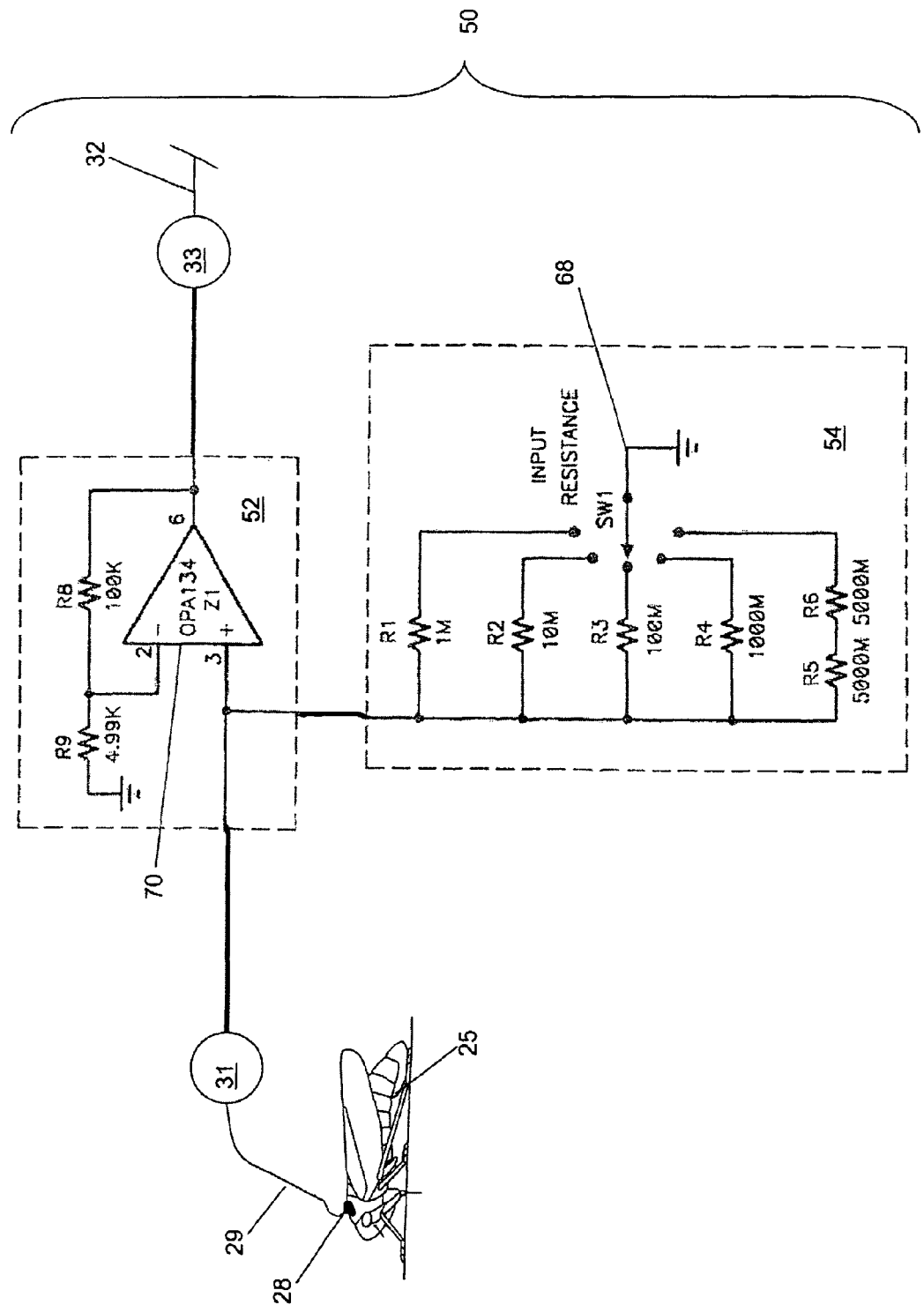
FIG. 6 is the circuit diagram of the of the head stage amplifier shown in FIG. 5.

As shown in FIGS. 5 and 6, the head amp system 50 comprises two primary assemblies: an operational amplifier assembly (i.e. "op amp assembly") 52 and a switched resistor assembly 54. The op amp assembly 52 and the switched resistor assembly 54 are coordinated to produce the best quality and most useful output signal.

Different insect species have varying levels of inherent electrical resistance/conductivity that are primarily a function of the size of the insect and the diameter of the insect's mouth parts. For the purposes of this application, "inherent resistance" is the electrical resistance (measured in ohms) evidenced by an insect placed in a simple direct current circuit.

The inventors have found that the clearest and most generally useful EPG waveform results are achieved when the head amp's selectable input resistance is essentially equal to the resistance level of the subject insect. However, the optimal instrument settings associated with a particular insect are generally derived through an iterative trial and error process. As shown in FIG. 6, the head amp design allows an operator to vary the input resistance through the switched resistor configuration to achieve the best possible result for the insect studied.

As shown in FIG. 6, in the preferred embodiment, the switched resistor assembly 54 is comprised of a circuit with five selectable resistance settings. Specifically, in the preferred embodiment, the switched resistor assembly is comprised of a circuit with R1 through R6 resistors having corresponding respective resistance values of 1 MΩ, 10 MΩ, 100 MΩ 1000 MΩ, 5000 MΩ, and 5000 MΩ. A resistance selection means such as a switch/rotary dial 68 (designated SW1 in FIG. 6) allows an operator to selectively switch between the respective head amp 50 resistance settings.

As indicated supra, the inventors have empirically determined that the most useful information can be gathered when the resistance value of the selected head amp input resistance setting is essentially equal to the resistance value of the subject insect 25. For example, if the studied insect 25 imparts a resistance of 1 MΩ, a switched resistance setting with a 1 MΩ resistance value 56 should be selected.

The inventors have also learned that the differing signals transmitted in response to the selection of different input resistance levels indicate information about varying aspects of the studied insect 25. For example, the signal associated with a high input resistance may indicate information regarding charges generated by the insect's own internal nervous and muscular system, while the selection of relatively low input resistance indicates information regarding the quality of the connection between the insect electrode 28 and the insect 25. Essentially, the configuration of the switched resistor assembly 54 allows an operator to tailor the settings of the head amp 50 to the particular insect and the specific behaviors being studied.

As shown in FIGS. 5 and 6 and discussed supra, in addition to the switched resistor assembly 54, the current invention also comprises an op amp assembly 52. The op amp assembly 52 receives the electrical signal from the insect 25 through an input terminal 31 and relays it through an output terminal 33 to the head amp cable 32 (see also FIG. 2). The purpose of the op amp assembly 52 is to receive, preserve, and amplify the signal from the insect 25. In the preferred embodiment, the op amp assembly 52 has again of about 20 so that the outgoing signal is amplified 20 times relative to the incoming signal. However, in alternative embodiments, the op amp assembly 52 may be designed so that the gain may be of any magnitude specified by a designer/operator.

As shown in FIG. 6, the op amp assembly 52 comprises an op amp component 70 designated Z1 as well as R8 and R9 resistors. In the preferred embodiment, the op amp 70 is an OPA134-type component and the R8 and R9 resistors have a resistance of 4.99 KΩ and 100 KΩ respectively. In alternative embodiments, the op amp assembly 52 may be comprised of any components or combination of components consistent with the functions described herein.

As generally shown in FIG. 2, the waveform voltage signal is transmitted from the head amp 50, through the output terminal 33 to the head amp cable 32 and through an input terminal 51 to an internal amplifier system (i.e. "internal amp" system) 80 located within the monitoring device 30.

Figure 7:
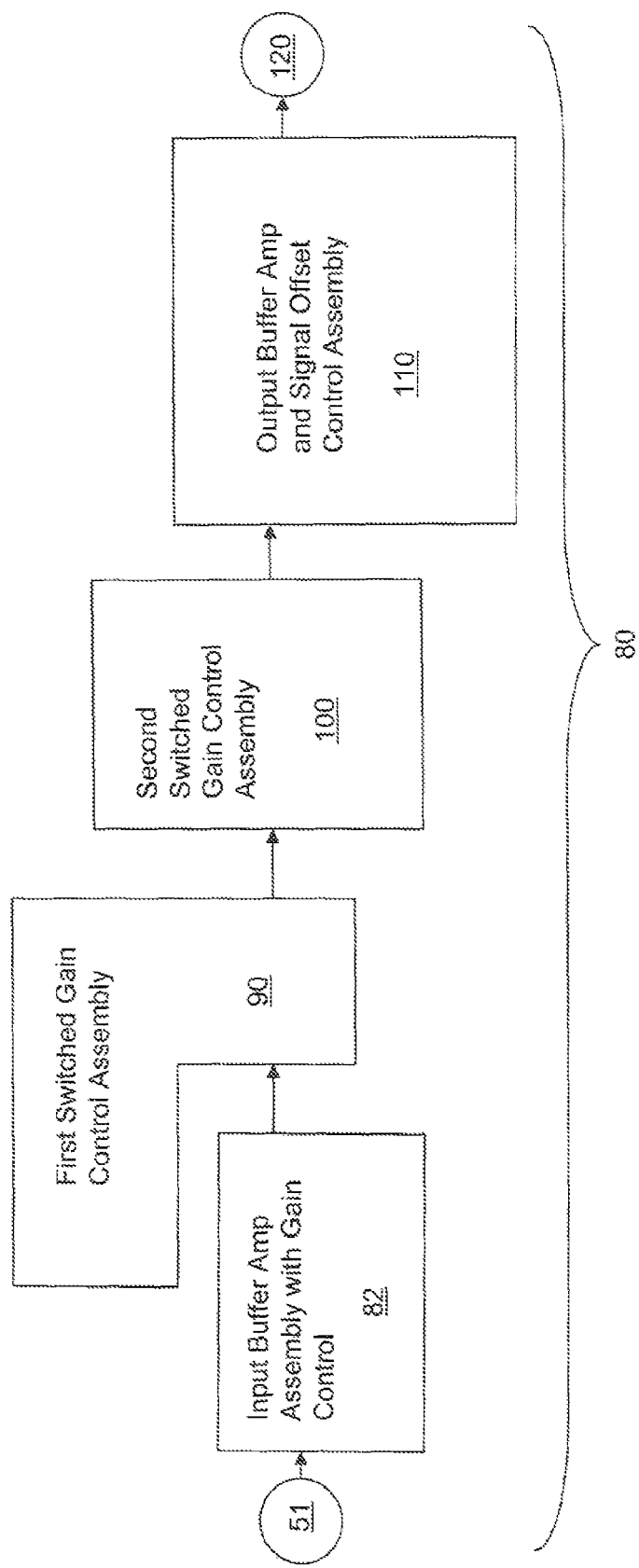
FIG. 7 is a block diagram of the internal amplifier of the improved monitoring system.
Figure 8:
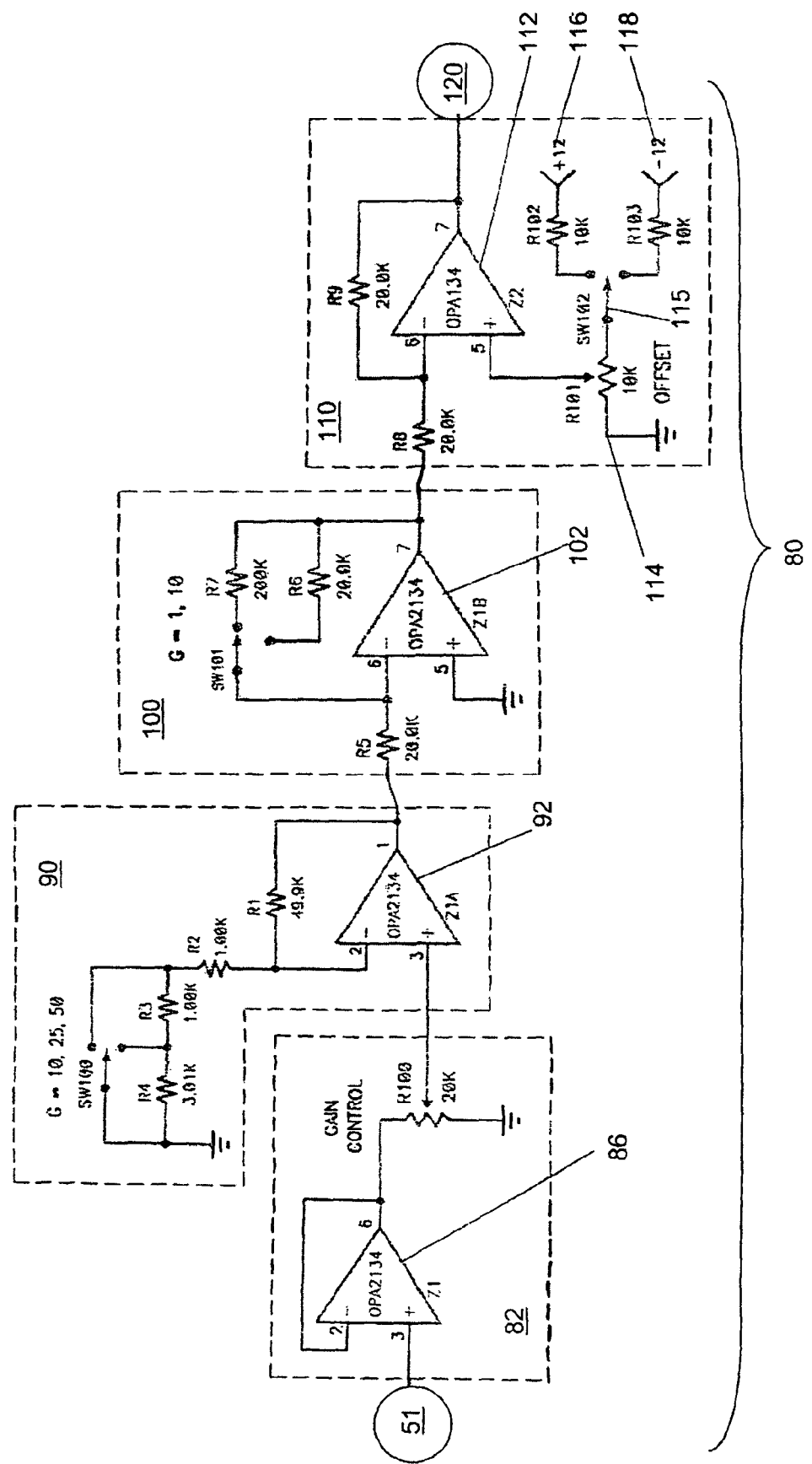
FIG. 8 is a circuit diagram of the internal amplifier shown in FIG. 7.

As shown in FIGS. 7 and 8, the internal amp system 80 is comprised of a chain of adjustable amplifier assemblies 82, 90, 100, 110 that allow an operator to adjust the gain and polarity of the output waveform signal. The amplified waveform signal is the transmitted through an output terminal 120.

As shown in FIG. 8, the waveform signal enters through an input terminal 51 and moves through an input buffer amplifier assembly 82 that includes an adjustable gain control 84. The Z1 input buffer amplifier component (i.e. "input buffer amp") 86 buffers the input signal from the head amp 50. In the preferred embodiment, the input buffer amp component 86 is comprised of an OPA2134-type component. The signal then proceeds to an adjustable resistor 84 (designated as R100 in FIG. 8) that functions as an adjustable gain control. In the preferred embodiment, the adjustable resistor 84 comprises an adjustable 20Ω resistor connected with a knob-type adjustment mechanism on the face of the monitoring device 30 that allows an operator to fine tune the internal amp assembly's 80 gain.

As shown in FIGS. 7 and 8, first 90 and second 100 switched gain control assemblies are connected to the input buffer amp assembly with adjustable gain control 84. The first gain control assembly 90 comprises an amplifier component 92 and a switched gain adjustment control component 94 designated SW100 as well as a series of resistors designated R1 through R4.

In the preferred embodiment, the switched gain control component 94 allows an operator to select a gain factor of 10, 25, or 50. In alternative embodiments the circuit may be arranged so that other gain settings are possible. Similarly, as shown in FIG. 8, the amplifier component 92 of the preferred embodiment is an OPA2134 amplifier and the resistance values of the R1 through R4 resistors are 49.9 KΩ, 1 KΩ, 1 KΩ, and 3.01 KΩ respectively. In alternative embodiments the amplifier component and the resistance values of the respective resistors may be altered to achieve a specific desired result.

As shown in FIGS. 7 and 8, the second gain control assembly 100 comprises an amplifier component 102 designated Z1B and a switched gain adjustment control component 104 designated SW101 as well as a series of resistors designated R5 through R7.

In the preferred embodiment, the switched gain control component 104 allows an operator to further increase the gain by a factor of 10 so that the total maximum amount of gain from the insect signal is a factor of 10,000. In alternative embodiments the circuit may be arranged so that other gain settings are possible. Similarly, as shown in FIG. 8, the amplifier component 102 of the preferred embodiment is an OPA2134 amplifier, and the resistance values of the R5 through R7 resistors are 20 KΩ, 20 kΩ, and 200 KΩ respectively. In alternative embodiments the amplifier component 102 and the resistance values of the respective resistors may be altered to achieve a specific desired result.

As further shown in FIGS. 7 and 8, an output buffer amplifier and signal offset control assembly 110 is connected to the first 90 and second 100 gain control assemblies. The output buffer amplifier (i.e. "output buffer amp") portion of the assembly 110 comprises an amplifier component 112 designated Z2 and associated resistors R8 and R9. The output buffer amp portion of the assembly 110 ensures that the internal amp assembly 80 is unaffected by changes on the output side of the internal amp assembly 80 that are exterior to the amp assembly 80.

In the preferred embodiment, the output buffer amp component 112 is comprised of an OPA134 amplifier and the R8 and R9 resistors both have resistance values of 20 kΩ. In alternative embodiments, the output buffer amp portion of the assembly 110 may be comprised of any alternative components or combination of components consistent with the functions as described herein.

The offset control portion of the assembly comprises a variable resistance resistor 114 (designated R101) and a voltage offset switch 115 (designated SW101) selectively connected to either a positive twelve volt power supply 116 and associated resistor R102, or a negative twelve volt power supply 118 and an associated resistor R103.

A switch associated with the voltage offset switch 115 is disposed on the front of the monitoring device 30 to allow an operator do adjust the offset in a positive or negative direction. A fine tune knob associated with the variable resistance resistor 114 is also disposed on the front of the monitoring device 30 (see FIG. 2) to allow an operator to allow an operator to further fine tune the offset. In operation, an operator may use the voltage offset switch 115 and the variable resistor 114 to ensure that the monitoring system waveform data is properly normalized to zero volts output prior to the initiation of an insect evaluation.

In the preferred embodiment the variable resistance resistor 114 is comprised of a 10 KΩ resistor and the R102 and R103 resistors are both comprised of 10 KΩ resistors. In alternative embodiments, the resistance values of the respective resistors may be varied as required consistent with the function of the current invention.

As shown in FIGS. 2, 7, and 8, the output buffer amplifier and signal offset control assembly 110 is connected to an output terminal 120. As shown in FIG. 2 and discussed supra, in the preferred embodiment, a portion of the output waveform signal is sent to a marking device 22 and then to a controller 20, and a portion of the signal is sent directly to the controller 20. In alternative embodiments, the output waveform signal may be sent directly to an output device(s) 24 or processed, recorded, and/or displayed as required.

For the foregoing reasons, it is clear that the current invention provides an improved EPG signal generating and processing device. The current invention may be modified and customized as required by a specific operation or application, and the individual components may be modified and defined, as required, to achieve the desired result. For example, although the invention was originally intended to monitor a feeding insect, the invention may be modified to monitor other organisms or phenomena.

Although the materials of construction are not described, they may include a variety of compositions consistent with the function of the invention. Such variations are not to be regarded as a departure from the spirit and scope of the invention, and all such modifications as would be obvious to one skilled in the art are intended to be included within the scope of the following claims.

What is claimed is:

1. A system for monitoring the feeding behavior of insects, the system comprising:
    an insect electrode, the insect electrode being attached to an insect feeding on a host plant;
    a head stage amplifier system, the head stage amplifier system being connected to the insect electrode, the head stage amplifier system comprising:
        (a) an operational amplifier assembly; and
        (b) a switched resistor assembly connected to the operational amplifier assembly, the switched resistor assembly comprising multiple selectable resistors yielding multiple selectable levels of input resistance for the head stage amplifier;
        (c) a resistance selection means enabling an operator to select one of the selectable resistors and thereby specify an input resistance for the head stage amplifier;
    wherein the operator connects the insect to the insect electrode and initiates an evaluation of the insect, the operator using the resistance selection means to select the input resistance of the head stage amplifier based on the insect.

2. The system of claim 1 wherein the operator selects a selectable resistor yielding an input resistance equal to an inherent resistance of the insect.

3. The system of claim 2 wherein the multiple selectable resistors yields five input resistance settings.

4. The system of claim 3 wherein the five input resistance settings are 1 MΩ, 10 MΩ, 100 MΩ, 1000 MΩ, and 10,000 MΩ.

5. The system of claim 1 wherein the operational amplifier assembly comprises an operational amplifier component.

6. The system of claim 1 wherein the head stage amplifier system imparts a gain of a factor of 20 to the head stage amplifier output signal.

7. The system of claim 1 wherein the head stage amplifier transmits voltage waveform data to a monitoring device.

8. The system of claim 7 wherein the monitoring device comprises a regulated and buffered direct current voltage source and a buffered internal amplifier, the monitoring device transmitting current to the insect and receiving the waveform signal from the head stage amplifier.

9. The system of claim 8 wherein the voltage source is comprised of reference diode.

10. The system of claim 9 wherein the reference diode is connected to a potentiometer.

11. The system of claim 10 wherein the potentiometer is connected to buffer amplifiers.

12. The system of claim 11 wherein the buffer amplifiers are operational amplifier components.

13. The system of claim 10 wherein the output of the buffer amplifiers are connected to a polarity switch and a potentiometer.

14. The system of claim 13 wherein the potentiometer is connected to an output buffer amplifier.

15. The system of claim 14 wherein the output buffer amplifier transmits current to the insect.

16. The system of claim 8 wherein the internal amplifier comprises a chain of amplifiers comprising an input buffer amplifier, at least one gain control amplifier, and an output buffer amplifier.

17. The system of claim 16 comprising at least two gain control amplifiers.

18. The system of claim 8 wherein the internal amplifier comprises an input buffer amplifier connected to a potentiometer.

19. The system of clam 18 wherein the buffer amplifier is an operational amplifier component.

20. The system of claim 18 wherein the potentiometer is connected to a first switched gain control assembly.

21. The system of claim 20 wherein the first switched gain control assembly boosts the output of the head stage amplifier waveform signal by a factor of 1, 10, 25, or 50.

22. The system of claim 21 wherein the first switched gain control assembly is comprised of an operational amplifier component.

23. The system of claim 20 wherein the first switched gain control assembly is connected to a second switched gain control assembly.

24. The system of claim 23 wherein the second switched gain control assembly boosts the output of the first switched gain control assembly by a factor of one of 1 or 10.

25. The system of claim 23 wherein the second gain control assembly is comprised of an operational component.

26. The system of claim 23 wherein the second switched gain control assembly is connected to an output buffer amplifier and signal offset control assembly.

27. The system of claim 26 wherein an output buffer amplifier portion of the buffer amplifier and signal offset control assembly is comprised of an operational component.

28. The system of claim 26 wherein the signal offset control portion of the buffer amplifier and signal offset control assembly is comprised of a potentiometer that is selectively connected to either a positive or a negative direct current voltage source.

29. The system of claim 26 wherein an output portion of the buffer amplifier and signal offset control assembly is connected to an output terminal of the monitoring device.

30. The system of claim 29 wherein the output terminal is connected to a marking device so that a portion of a monitoring device output waveform voltage signal is transmitted to the marking device.

31. A system for monitoring the behavior of an organism, the system comprising:
 a monitoring device;
 a regulated and buffered direct current voltage source, the voltage being disposed within the monitoring device;
 a plant electrode, the plant electrode being positioned on or adjacent to a host plant, the plant electrode receiving an electrical current from the voltage source;
 an insect electrode, the insect electrode being positioned on an insect disposed on the host plant, the insect electrode receiving a waveform voltage signal from the insect;
 a head stage amplifier, the head stage amplifier receiving the waveform voltage signal from the insect electrode, the head stage amplifier comprising an adjustable resistance means and an amplifying means, the head stage amplifier amplifying the waveform voltage signal;
 an internal amplifier, the internal amplifier being connected to the head stage amplifier and disposed within the monitoring device, the internal amplifier comprising:
  (a) an input buffer amplifier;
  (b) at least one gain control amplifier connected to the input buffer amplifier;
  (c) a signal offset control connected to the at least one gain control amplifier; and
  (d) an output buffer amp;
 wherein an operator directs current from the voltage source through the host plant, the insect, and the insect electrode, the insect electrode also receiving the associated waveform voltage signal, the head stage amplifier receiving the signal from the insect electrode, the head stage amplifier amplifying the signal and directing the signal through the internal amplifier to a display device.

* * * * *